United States Patent [19]

Plate

[11] Patent Number: 5,470,856
[45] Date of Patent: Nov. 28, 1995

[54] TETRAHYDROPYRIMIDINE DERIVATIVES

[75] Inventor: Ralf Plate, Oss, Netherlands

[73] Assignee: Akzo Nobel N.V., Arnhem, Netherlands

[21] Appl. No.: 25,707

[22] Filed: Mar. 3, 1993

[30] Foreign Application Priority Data

Apr. 3, 1992 [EP] European Pat. Off. .............. 92200622

[51] Int. Cl.$^6$ ..................... C07D 239/48; C07D 239/42; A61K 31/505
[52] U.S. Cl. .......................... 514/256; 514/275; 544/323; 544/332
[58] Field of Search .................................. 514/256, 275; 544/323, 332

[56] References Cited

FOREIGN PATENT DOCUMENTS

| 0271798 | 6/1988 | European Pat. Off. . |
| 0309425 | 3/1989 | European Pat. Off. . |
| 0445731 | 9/1991 | European Pat. Off. . |

OTHER PUBLICATIONS

Evans, J. Chem. Soc, pp. 2450–2455 (1964).

Primary Examiner—John M. Ford
Attorney, Agent, or Firm—Mary E. Gormley

[57] ABSTRACT

The invention is concerned with a tetrahydropyrimidine derivative having formula I

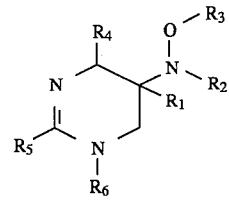

wherein
  $R_1$ is hydrogen;
  $R_2$ is hydrogen, a lower alkyl group, or lower acyl; or
  $R_1$ and $R_2$ represent together a bond;
  $R_3$ is hydrogen, a lower hydrocarbon group optionally substituted with halogen, CN, aryl, or $COR_7$;
  $R_4$ is hydrogen, a lower alk(en)yl group, or aryl;
  $R_5$ is hydrogen, amino, lower alkyl substituted amino, or a lower alkyl group; and
  $R_6$ is hydrogen or methyl;
  $R_7$ is amino, lower alkyl substituted amino, or a lower alkyl group; or
a pharmaceutically acceptable salt thereof.

The compounds of this invention have muscarinic properties and can be used for the treatment of cognition disorders, and for the treatment of cholinergic deficiencies.

12 Claims, No Drawings

TETRAHYDROPYRIMIDINE DERIVATIVES

The invention relates to tetrahydropyrimidine derivatives, a process for the preparation thereof, a pharmaceutical composition containing the same, as well as to the use of these tetrahydropyrimidine derivatives for the preparation of a medicament.

BACKGROUND THE INVENTION

Related compounds, i.e. 4-piperidinone oxime derivatives, are described in European patent application 445,731. The muscarinic agonist potency of the present compounds is, however, considerably higher than the potency of the known 4-piperidinone oxime derivatives, especially with respect to the important M1 and M3 muscarinic subtypes.

BRIEF DESCRIPTION OF THE INVENTION

The present invention relates to a tetrahydropyrimidine derivative having formula I

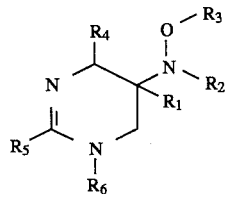

wherein $R_1$ is hydrogen;

$R_2$ is hydrogen, a lower alkyl group, or lower acyl; or $R_1$ and $R_2$ represent together a bond;

$R_3$ is hydrogen, a lower hydrocarbon group optionally substituted with halogen, CN, aryl or $COR_7$;

$R_4$ is hydrogen, a lower alk(en)yl group, or aryl;

$R_5$ is hydrogen, amino, lower alkyl substituted amino, or a lower alkyl group; and $R_6$ is hydrogen or methyl;

$R_7$ is amino, lower alkyl substituted amino, or a lower alkyl group; or a pharmaceutically acceptable salt thereof.

DETAILED DESCRIPTION OF THE INVENTION

The compounds of this invention have muscarinic properties. They bind to muscarinic agonist receptor sites with a 2 to 750 fold preference as compared to muscarinic antagonist receptor sites, as is exemplified in their ability to bind preferentially to the agonist site of muscarinic receptors in membrane preparations of rat cerebral cortex, or membrane from rat forebrain. Preferred compounds show an agonist/antagonist binding ratio of between 10 and 400.

The tetrahydropyrimidine derivatives are suitable for the treatment of cognition disorders, like presenile and senile dementia, including Alzheimer's disease, learning and memory disturbances, and for the treatment of other cholinergic deficiencies, like Huntington's chorea, tardive dyskinesia, hyperkinesia, mania, and Tourette syndrome or similar conditions characterized by a decrease in cerebral acetylcholine production or release. The compounds of the invention are useful for the treatment of glaucoma and as analgetic agents for the treatment of pain in mammals, including man.

Preferred compounds according to the invention are the tetrahydropyrimidine derivative of formula I, in which $R_1$ and $R_2$ represent together a bond, and $R_3$ is a (1–3 C) hydrocarbon group, and more preferably methyl, ethyl, or 2-propynyl, and $R_5$ and $R_6$ are hydrogen, or a pharmaceutically acceptable salt thereof.

The term lower acyl means an acyl group derived from an aliphatic carboxylic acid having preferably 2–6 carbon atoms, like acetyl, propanoyl, or butanoyl.

The term lower hydrocarbon group means a branched or unbranched, cyclic or acyclic, saturated or unsaturated aliphatic hydrocarbon group having preferably 1–18 carbon atoms. More preferred are hydrocarbon groups having 1–12 carbon atoms. Examples are methyl, ethyl, propyl, sec-butyl, vinyl, 2-propenyl, ethynyl, 2-propynyl, 2-butynyl, 3-methyl-2-penten-4-ynyl, 3-hexynyl, nona-2,5,8-triynyl, cyclopentyl, and cyclohexyl. Preferred are hydrocarbon groups having 1–3 carbon atoms, and more preferred the unbranched hydrocarbon groups having 1–3 carbon atoms. Most preferred are the methyl, ethyl, 2-propenyl, and 2-propynyl groups.

The term halogen means F, Cl, Br or I. When halogen is a substituent at a lower hydrocarbon group, Cl and F are preferred, F being most preferred.

The term lower alkyl means a branched or unbranched alkyl group having preferably 1–6 carbon atoms, like hexyl, isobutyl, propyl, ethyl, and, preferably, methyl.

The term lower alk(en)yl means a lower alkyl group as previously defined or a lower alkenyl group having preferably 1–6 carbon atoms, like 2-propenyl, vinyl, 2-butenyl, 1,3-butadienyl, or 2-methyl-1-propenyl.

The term aryl means a phenyl group which may be substituted with OH, F, Cl, Br, $CF_3$, CN, lower alkyl, and/or lower alkoxy.

The term lower alkoxy means an alkoxy group derived from a lower alkyl group as previously defined.

The novel compounds of formula I may be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention may possess a chiral carbon atom, and may therefore be obtained as a pure enantiomer, or as a mixture of enantiomers, among which the racemic mixture. Methods for obtaining the pure enantiomers are well known in the art, e.g. synthesis from chirally pure 3-azabicyclo-alkanol or crystallization of salts which are obtained from optically active acids and the racemic mixture, or chromatography using chiral columns.

Preferred compounds according to this invention have formula I, in which $R_1$ and $R_2$ represent together a bond, and $R_3$ is a (1–3 C) hydrocarbon group. More preferred are those compounds in which $R_3$ is ethyl or 2-propynyl and $R_4$, $R_5$, and $R_6$ are hydrogen, or a pharmaceutically acceptable salt thereof.

The tetrahydropyrimidine derivatives of the invention can be prepared by methods known for the preparation of analogous compounds.

A suitable method is the condensation of an amine having the formula $NH_2OR_3$, in which $R_3$ has the previously given meaning, with a 1,6-dihydro-5(4H)-pyrimidinone having the formula II, in which $R_4$, $R_5$, and $R_6$ have the previously given meanings.

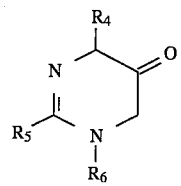

The unsaturated bond of the condensation product may be saturated by methods known for the saturation of imides (particularly when $R_1$ is hydrogen), like borohydride (preferably trimethylamine borohydride) reductions, after which the hydrogen atom attached to the nitrogen atom may optionally be substituted by a group $R_2$, by methods commonly in use for the alkylation or acylation of nitrogen atoms. A suitable method is the acylation with $R_2$'COHal, in which Hal is a halogen atom like chlorine, and $R_2$'CO is $R_2$ when its meaning is lower acyl.

Compounds of formula I in which $R_1$ and $R_2$ are not together a bond, can also be prepared by condensation of an amine $NHR_2OR_3$, in which $R_2$ and $R_3$ have the previously given meanings, and a compound having formula III

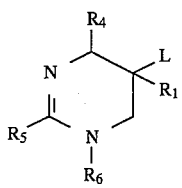

in which L denotes a leaving group like a halide, such as chlorine, bromine, or fluorine, or a sulfonyloxy group, such as tosyl- or mesyloxy, and $R_1$, $R_4$, $R_5$, and $R_6$ have the previously given meanings.

Compounds of formula III may be obtained from 1,6-dihydro-5(4H)-pyrimidinone having formula II, by reduction of the keto group into a hydroxy group, using standard methods well known to the skilled organic chemist, or by a Grignard-type reaction introducing simultaneously the group $R_1$, followed by conversion of the hydroxy group of the thus obtained 5-tetrahydropyrimidinol derivatives into a leaving group by customary methods, such as reaction with thionylchloride, phosphorous tribromide, tosylchloride, and the like.

Another method for the preparation of compounds of formula I in which $R_1$ and $R_2$ together are a bond, is the condensation of an oxime having formula IV

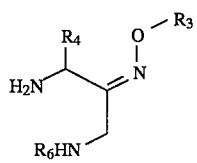

wherein $R_3$, $R_4$, and $R_6$ have the previously given meanings with an orthoformate derivative having the formula (Alkyl—O)$_3$C—$R_5$, wherein $R_5$ has the previously defined meaning and Alkyl is an alkyl group as previously defined for lower alkyl, and peferably methyl.

The compounds of the invention may be administered enterally or parenterally, and for humans preferably in a daily dosage of 0.001–10 mg per kg body weight. Mixed with pharmaceutically suitable auxiliaries, e.g. as described in the standard reference, Gennaro et al., Remington's Pharmaceutical Sciences (18th ed., Mack Publishing company, 1990, see especially Part 8: pharmaceutical Preparations and Their Manufacture), the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray. A further application of the compounds of the invention is in the manufacture of ophthalmic preparations, which include solutions, suspensions, ointments and solid dosage forms. For making dosage units, e.g. tablets, the use of conventional additives such as fillers, colorants, polymeric binders and the like is contemplated. In general any pharmaceutical acceptable additive which does not interfere with the function of the active compounds can be used. Suitable carriers with which the compositions can be administered include lactose, starch, cellulose derivatives and the like, or mixtures thereof, used in suitable amounts.

The invention is further illustrated by the following examples.

EXAMPLE 1

1,6-Dihydro-5(4H)-pyrimidinone O-methyloxime monohydrochloride 1,3-Diaminoacetone dihydrochloride monohydrate (2.61 g, 14.6 mmol) was dissolved in refluxing methanol. To this solution o-methylhydroxylamine hydrochloride (2.43 g, 29.2 mmol) was added. After reflexing for 48 hours the solvents were evaporated. The crude product was dissolved in methanol and an excess of trimethylorthoformate was added to the reaction mixture which was heated to reflux. After 24 hours the solvent was removed in vacuo. crystallization from methanol/ethyl acetate afforded 850 mg (36%) of a light-brown crystalline material. Mp. 170.7° C.

EXAMPLE 2

1,6-Dihydro-5(4H)-pyrimidinone O-ethyloxime monohydrochloride 1,3-Diaminoacetone dihydrochloride monohydrate (5.00 g, 7.9 mmol) was dissolved in refluxing methanol and o-ethylhydroxylamine hydrochloride (5.44 g, 55.8 mmol) was added. After refluxing for 48 hours the solvent was evaporated. The crude product was dissolved in methanol and an excess of trimethylorthoformate was added to the reaction mixture which was heated to reflux. After 24 hours the solvent was removed in vacuo. crystallization from methanol/ethyl acetate afforded 2.30 g (48%) light-brown material. Mp. 163.8° C.

EXAMPLE 3

1,6-Dihydro-5(4H)-pyrimidinone O-(2-propynyl)oxime monohydrochloride 1,3-diaminoacetone dihydrochloride monohydrate (1.10 g, 6.14 mmol) was dissolved in refluxing methanol and O-(2-propynyl)hydroxylamine hydrochloride (0.730 g, 6.75 mmol) was added. After refluxing for 48 hours the solvent was evaporated. The crude product was dissolved in methanol and an excess of trimethylorthoformate was added to the reaction mixture and heated to reflux. After 24 hours the solvent was removed in vacuo. Crystallization from methanol/ethyl acetate afforded 410 mg (36%) of light-brown material. Mp. 205.0° C.

EXAMPLE 4

1,6-Dihydro-5(4H)-pyrimidinone O-(1-methylethyl)oxime monohydrochloride 1,3-Diaminoacetone dihydrochloride monohydrate (2.0 g, 11.2 mmol) was dissolved in refluxing methanol and O-(1-methylethyl)hydroxylamine hydrochloride (2.5 g, 22.4 mmol) was added. After refluxing for 48 hours the solvent was evaporated. The crude product was dissolved in methanol and an excess of trimethylorthoformate was added to the reaction mixture which was heated to reflux. After 24 hours the solvent was removed in Vacuo. Crystallization from methanol/ethyl acetate afforded 1.00 g (47%) light-brown material. Mp. 170.0° C.

EXAMPLE 5

1,6-Dihydro-5(4H)-pyrimidinone O-(cyclopropylmethyl)-oxime monohydrochloride 1,3-Diaminoacetone dihydrochloride monohydrate (2.00 g, 11.2 mmol) was dissolved in refluxing methanol and O-(cyclopropylmethyl)hydroxylamine hydrochloride (2.60 g, 21.1 mmol) was added. After refluxing for 96 hours the solvent was evaporated. The crude product was dissolved in methanol and an excess of trimethylorthoformate was added to the reaction mixture which was heated to reflux. After 48 hours the solvent was removed in vacuo. Crystallization from methanol/ethyl acetate afforded 1.30 g (57%) of light-brown material. Mp. 158.0° C.

EXAMPLE 6

1,6-Dihydro-5(4H)-pyrimidinone O-(2-propenyl)oxime monohydrochloride 1,3-Diaminoacetone dihydrochloride monohydrate (2.00 g, 11.2 mmol) was dissolved in refluxing methanol and O-2-propenylhydroxylamine hydrochloride (2.40 g, 21.9 mmol) was added. After refluxing for 96 hours the solvent was evaporated. The crude product was dissolved in methanol and an excess of trimethylorthoformate was added to the reaction mixture which was heated to reflux. After 48 hours the solvent was removed in vacuo. Crystallization from methanol/ethyl acetate afforded 1.20 g (57%) of white material. Mp. 164.5° C.

EXAMPLE 7

1,6-Dihydro-5(4H)-pyrimidinone O-(phenylmethyl)oxime monohydrochloride 1,3-Diaminoacetone dihydrochloride monohydrate (2.00 g, 11.2 mmol) was dissolved in refluxing methanol and O-phenylmethylhydroxylamine hydrochloride (3.30 g, 20.5 mmol) was added. After refluxing for 20 hours the solvent was evaporated. The crude product was dissolved in methanol and an excess of trimethylorthoformate was added to the reaction mixture which was heated to reflux. After 48 hours the solvent was removed in vacuo. Crystallization from methanol/ethyl acetate afforded 1.60 g (60%) of white material. Mp. 167.5° C.

EXAMPLE 8

In a similar manner as described in examples 1–7 were prepared:

1,6-Dihydro-5(4H)-pyrimidinone O-(1,1-dimethylethyl)oxime monohydrochloride. M.p. 199° C.

1,6-Dihydro-4-methyl-5(4H)-pyrimidinone O-ethyloxime monohydrochloride. M.p. 153° C.

1,6-Dihydro-5(4H)-pyrimidinone O-[(2-chlorophenyl)methyl] oxime monohydrochloride. M.p. 187° C.

1,6-Dihydro-5(4H)-pyrimidinone O-[(2-fluorophenyl)methyl]oxime monohydrochloride. M.p. 176° C.

1,6-Dihydro-5(4H)-pyrimidinone O-[(2-trifluoromethylphenyl)methyl]oxime monohydrochloride. M.p. 176° C.

1,6-Dihydro-5(4H)-pyrimidinone O-propyloxime monohydrochloride. M.p. 147° C.

1,6-Dihydro-5(4H)-pyrimidinone O-(1-methylpropyl)oxime monohydrochloride. M.p. 178° C.

1,6-Dihydro-5(4H)-pyrimidinone O-(3-phenyl-2-propynyl)oxime monohydrochloride. M.p. 168° C.

1,6-Dihydro-2-methyl-5(4H)-pyrimidinone O-(2-propenyl)oxime monohydrochloride. M.p. 135° C.

1,6-Dihydro-5(4H)-pyrimidinone O-(2-butynyl)oxime monohydrochloride. M.p. 176° C.

(E)1,6-Dihydro-5(4H)-pyrimidinone O-(3-methyl-2-penten-4-ynyl)oxime monohydrochloride. M.p. 186° C.

1,6-Dihydro-5(4H)-pyrimidinone O-(2-butenyl)oxime monohydrochloride. M.p. 136° C.

1,6-Dihydro-5(4H)-pyrimidinone O-(nona-2,5,8-triynyl)oxime monohydrochloride.

1,6-Dihydro-5(4H)-pyrimidinone O-butyloxime monohydrochloride. M.p. 145° C.

1,6-Dihydro-5(4H)-pyrimidinone O-(3-hexynyl)oxime monohydrochloride.

1,6-Dihydro-5(4H)-pyrimidinone O-(2-methoxy-2-oxoethyl)oxime monohydrochloride. M.p. 167° C.

1,6-Dihydro-5(4H)-pyrimidinone O-phenyloxime monohydrochloride 1,6-Dihydro-5(4H)-pyrimidinone O-(cyanomethyl)oxime monohydrochloride 1,6-Dihydro-5(4H)-pyrimidinone O-acetyloxime monohydrochloride 1,6-Dihydro-5(4H)-pyrimidinone O-carbamoyloxime monohydrochloride

EXAMPLE 9

1,4,5,6-Tetrahydro-N-methoxy-5-pyrimidinamine dihydrochloride

A solution of 1,6-dihydro-5-(4H)-pyrimidinone O-methyloxim monohydrochloride (2.8 g, 17.1 mmol) in dry methanol was added dropwise to a stirred solution of HCl/methanol (49 ml of a 3N solution) and trimethylamine borohydride (1.36 g, 18.7 mmol) at room temperature under a nitrogen atmosphere. After 1 hour the reaction product crystallised spontaneously. Recrystallization from methanol/ethyl acetate gave a light-brown material in 38% yield (1.30 g). Mp. 214.0° C.

EXAMPLE 10

In a similar manner as described in example 9 was prepared 1,4,5,6-Tetrahydro-N-ethoxy-5-pyrimidinamine dihydrochloride. M.p. 178° C.

I claim:

1. A tetrahydropyrimidine derivative having formula I

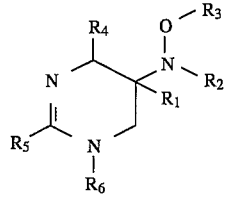

wherein $R_1$ is hydrogen;

$R_2$ is selected from the group consisting of hydrogen, a lower alkyl group having 1 to 6 carbon atoms, and a lower acyl group derived from an aliphatic carboxylic acid having 2 to 6 carbon atoms;

or $R_1$ and $R_2$ represent together a bond;

$R_3$ is selected from the group consisting of hydrogen, $COR_7$ and a lower hydrocarbon group containing 1–18 carbon atoms and optionally substituted with halogen, CN, alkoxycarbonyl, phenyl or a phenyl group substituted with a substituent selected from the group consisting of OH, F, Cl, Br, $CF_3$, lower alkyl and lower alkoxy;

$R_4$ is selected from the group consisting of hydrogen, a lower alkyl group, a lower alkenyl group having 1 to 6 carbon atoms, phenyl or a phenyl group substituted with a substituent selected from the group consisting of OH, F, CL, BR, $CF_3$, lower alkyl and lower alkoxy;

$R_5$ is selected from the group consisting of hydrogen, amino, lower alkyl substituted amino, and a lower alkyl group; and $R_6$ is hydrogen or methyl, provided that when $R_1$ and $R_2$ together represent a bond and $R_3$, $R_4$ and $R_5$ are hydrogen, $R_6$ is methyl;

$R_7$ is selected from the group consisting of amino, lower akyl-substituted amino, and a lower alkyl group; or a pharmaceutically acceptable salt thereof.

2. The tetrahydropyrimidine derivative of claim 1, wherein $R_1$ and $R_2$ represent together a bond, and $R_3$ is a hydrocarbon group with 1 to 3 carbons.

3. The tetrahydropyrimidine derivative of claim 2, wherein $R_3$ is ethyl and $R_4$, $R_5$, and $R_6$ are hydrogen.

4. The tetrahydropyrimidine derivative of claim 2, wherein $R_3$ is 2-propynyl and $R_4$, $R_5$, and $R_6$ are hydrogen.

5. A pharmaceutical composition comprising a pharmaceutically effective amount of the tetrahydropyrimidine derivative of claim 1 in admixture with pharmaceutically acceptable auxiliaries.

6. A method of treating cholinergic deficiencies comprising administering a pharmaceutical composition according to claim 5 to a person with said deficiencies.

7. A pharmaceutical composition comprising a pharmaceutically effective amount of the tetrahydropyrimidine derivative of claim 2 in admixture with pharmaceutically acceptable auxiliaries.

8. A pharmaceutical composition comprising a pharmaceutically effective amount of the tetrahydropyrimidine derivative of claim 3 in admixture with pharmaceutically acceptable auxiliaries.

9. A pharmaceutical composition comprising a pharmaceutically effective amount of the tetrahydropyrimidine derivative of claim 4 in admixture with pharmaceutically acceptable auxiliaries.

10. A method of treating cholinergic deficiencies comprising administering a pharmaceutical composition according to claim 7 to a person with said deficiencies.

11. A method of treating cholinergic deficiencies comprising administering a pharmaceutical composition according to claim 8 to a person with said deficiencies.

12. A method of treating cholinergic deficiencies comprising administering a pharmaceutical composition according to claim 9 to a person with said deficiencies.

* * * * *